US008303651B1

(12) United States Patent
Pacetti

(10) Patent No.: US 8,303,651 B1
(45) Date of Patent: Nov. 6, 2012

(54) POLYMERIC COATING FOR REDUCING THE RATE OF RELEASE OF A THERAPEUTIC SUBSTANCE FROM A STENT

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1167 days.

(21) Appl. No.: 09/948,513

(22) Filed: Sep. 7, 2001

(51) Int. Cl.
A61F 2/06 (2006.01)
(52) U.S. Cl. ...................... 623/1.46; 623/1.42
(58) Field of Classification Search ........ 623/1.42–1.46, 623/1.15; 424/422
See application file for complete search history.

(56) References Cited

U.S. PATENT DOCUMENTS

| | | | | |
|---|---|---|---|---|
| 2,072,303 A | 3/1937 | Herrmann et al. | ......... | 128/335.5 |
| 2,386,454 A | 10/1945 | Frosch et al. | .................... | 260/78 |
| 3,178,399 A | 4/1965 | Lo | | |
| 3,773,737 A | 11/1973 | Goodman et al. | .............. | 260/78 |
| 3,849,514 A | 11/1974 | Gray, Jr. et al. | ................ | 260/857 |
| 4,226,243 A | 10/1980 | Shalaby et al. | ............ | 128/335.5 |
| 4,329,383 A | 5/1982 | Joh | ................. | 428/36 |
| 4,343,931 A | 8/1982 | Barrows | ....................... | 528/291 |
| 4,459,380 A * | 7/1984 | Vostovich | ....................... | 524/94 |
| 4,529,792 A | 7/1985 | Barrows | ....................... | 528/291 |
| 4,611,051 A | 9/1986 | Hayes et al. | ................ | 528/295.3 |
| 4,656,242 A | 4/1987 | Swan et al. | ................ | 528/295.3 |
| 4,733,665 A | 3/1988 | Palmaz | ........................ | 128/343 |
| 4,800,882 A | 1/1989 | Gianturco | .................... | 128/343 |
| 4,816,339 A | 3/1989 | Tu et al. | | |
| 4,882,168 A | 11/1989 | Casey et al. | .................... | 424/468 |
| 4,886,062 A | 12/1989 | Wiktor | ......................... | 128/343 |
| 4,916,193 A | 4/1990 | Tang et al. | | |
| 4,931,287 A | 6/1990 | Bae et al. | ...................... | 424/484 |
| 4,941,870 A | 7/1990 | Okada et al. | .................... | 600/36 |
| 4,977,901 A | 12/1990 | Ofstead | ......................... | 128/772 |
| 5,019,096 A | 5/1991 | Fox, Jr. et al. | ..................... | 623/1 |
| 5,100,992 A | 3/1992 | Cohn et al. | .................... | 424/501 |
| 5,112,457 A | 5/1992 | Marchant | ....................... | 204/165 |
| 5,133,742 A | 7/1992 | Pinchuk | ......................... | 623/1 |
| 5,163,952 A | 11/1992 | Froix | .............................. | 623/1 |
| 5,165,919 A | 11/1992 | Sasaki et al. | .................. | 424/488 |
| 5,219,980 A | 6/1993 | Swidler | ......................... | 528/272 |
| 5,258,020 A | 11/1993 | Froix | .............................. | 623/1 |
| 5,272,012 A | 12/1993 | Opolski | ...................... | 428/423.1 |
| 5,292,516 A | 3/1994 | Viegas et al. | ................. | 424/423 |
| 5,298,260 A | 3/1994 | Viegas et al. | ................. | 424/486 |
| 5,300,295 A | 4/1994 | Viegas et al. | ................. | 424/427 |
| 5,306,501 A | 4/1994 | Viegas et al. | ................. | 424/423 |
| 5,306,786 A | 4/1994 | Moens et al. | ................. | 525/437 |
| 5,328,471 A | 7/1994 | Slepian | ........................ | 604/101 |
| 5,330,768 A | 7/1994 | Park et al. | ...................... | 424/501 |
| 5,380,299 A * | 1/1995 | Fearnot et al. | ................. | 604/265 |
| 5,417,981 A | 5/1995 | Endo et al. | ..................... | 424/486 |
| 5,447,724 A | 9/1995 | Helmus et al. | ................ | 424/426 |
| 5,455,040 A | 10/1995 | Marchant | ....................... | 424/426 |
| 5,462,990 A | 10/1995 | Hubbell et al. | .............. | 525/54.1 |
| 5,464,650 A | 11/1995 | Berg et al. | ....................... | 427/2.3 |
| 5,485,496 A | 1/1996 | Lee et al. | .......................... | 378/64 |
| 5,502,158 A | 3/1996 | Sinclair et al. | | |
| 5,516,781 A | 5/1996 | Morris et al. | | |
| 5,516,881 A | 5/1996 | Lee et al. | ....................... | 528/320 |
| 5,563,145 A | 10/1996 | Failli | | |
| 5,569,463 A | 10/1996 | Helmus et al. | ................ | 424/426 |
| 5,578,073 A | 11/1996 | Haimovich et al. | ............... | 623/1 |
| 5,584,877 A | 12/1996 | Miyake et al. | .................... | 623/1 |
| 5,605,696 A | 2/1997 | Eury et al. | ..................... | 424/423 |
| 5,607,467 A | 3/1997 | Froix | ................................ | 623/1 |
| 5,609,629 A | 3/1997 | Fearnot et al. | .................... | 623/1 |
| 5,610,241 A | 3/1997 | Lee et al. | ....................... | 525/411 |
| 5,616,338 A | 4/1997 | Fox, Jr. et al. | ................. | 424/423 |
| 5,624,411 A | 4/1997 | Tuch | ............................. | 604/265 |
| 5,628,730 A | 5/1997 | Shapland et al. | ................ | 604/21 |
| 5,644,020 A | 7/1997 | Timmermann et al. | ........ | 528/288 |
| 5,649,977 A | 7/1997 | Campbell | .......................... | 623/1 |
| 5,658,995 A | 8/1997 | Kohn et al. | .................... | 525/432 |
| 5,667,767 A | 9/1997 | Greff et al. | .................. | 424/9.411 |
| 5,670,558 A | 9/1997 | Onishi et al. | .................. | 523/112 |
| 5,674,242 A | 10/1997 | Phan et al. | ..................... | 606/198 |
| 5,679,400 A | 10/1997 | Tuch | ............................. | 427/2.14 |
| 5,700,286 A | 12/1997 | Tartaglia et al. | .................. | 623/1 |
| 5,702,754 A | 12/1997 | Zhong | .......................... | 427/2.12 |

(Continued)

FOREIGN PATENT DOCUMENTS

DE 42 24 401 1/1994

(Continued)

OTHER PUBLICATIONS

Khang et al., "Directed Osteoblast Functions on Micro-aligned Patterns of Carbon Nanofibers on a Polymer Matrix", Rev.Adv.Mater. Sci. 10 (2005) pp. 206-208.*

(Continued)

*Primary Examiner* — Kathleen Sonnett
*Assistant Examiner* — Sarah Webb
(74) *Attorney, Agent, or Firm* — Squire Sanders (US) LLP

(57) ABSTRACT

A stent for delivery of a therapeutic agent is disclosed. The stent includes a polymer coating for reducing the rate of release of the therapeutic agent. The polymer has a crystalline structure wherein the polymer is capable of significantly maintaining the crystalline lattice structure while the therapeutic agent is released from the stent such that the aqueous environment to which the stent is exposed subsequent to the implantation of the stent does not significantly convert the crystalline lattice structure of the polymer to an amorphous structure.

18 Claims, No Drawings

U.S. PATENT DOCUMENTS

| | | | | |
|---|---|---|---|---|
| 5,711,958 | A | 1/1998 | Cohn et al. | 424/423 |
| 5,716,981 | A | 2/1998 | Hunter et al. | 514/449 |
| 5,718,159 | A | 2/1998 | Thompson | |
| 5,721,131 | A | 2/1998 | Rudolph et al. | 435/240 |
| 5,723,219 | A | 3/1998 | Kolluri et al. | 428/411.1 |
| 5,735,897 | A | 4/1998 | Buirge | 623/12 |
| 5,746,998 | A | 5/1998 | Torchilin et al. | 424/9.4 |
| 5,756,553 | A * | 5/1998 | Iguchi et al. | 514/772.3 |
| 5,759,205 | A | 6/1998 | Valentini | 623/16 |
| 5,776,184 | A | 7/1998 | Tuch | 623/1 |
| 5,783,657 | A | 7/1998 | Pavlin et al. | 528/310 |
| 5,788,979 | A | 8/1998 | Alt et al. | 424/426 |
| 5,800,392 | A | 9/1998 | Racchini | 604/96 |
| 5,820,917 | A | 10/1998 | Tuch | 427/2.1 |
| 5,824,048 | A | 10/1998 | Tuch | |
| 5,824,049 | A | 10/1998 | Ragheb et al. | 623/1 |
| 5,830,178 | A | 11/1998 | Jones et al. | 604/49 |
| 5,837,008 | A | 11/1998 | Berg et al. | 623/1 |
| 5,837,313 | A * | 11/1998 | Ding et al. | 427/2.21 |
| 5,849,859 | A | 12/1998 | Acemoglu | 528/271 |
| 5,851,508 | A | 12/1998 | Greff et al. | 424/9.411 |
| 5,854,376 | A | 12/1998 | Higashi | 528/288 |
| 5,858,746 | A | 1/1999 | Hubbell et al. | 435/177 |
| 5,865,814 | A | 2/1999 | Tuch | 604/265 |
| 5,869,127 | A * | 2/1999 | Zhong | 427/2.12 |
| 5,871,436 | A * | 2/1999 | Eury | 600/3 |
| 5,873,904 | A | 2/1999 | Ragheb et al. | 623/1 |
| 5,876,433 | A | 3/1999 | Lunn | 623/1 |
| 5,877,224 | A | 3/1999 | Brocchini et al. | 514/772.2 |
| 5,879,713 | A | 3/1999 | Roth et al. | 424/489 |
| 5,902,875 | A | 5/1999 | Roby et al. | 528/310 |
| 5,905,168 | A | 5/1999 | Dos Santos et al. | 562/590 |
| 5,910,564 | A | 6/1999 | Gruning et al. | 528/310 |
| 5,914,387 | A | 6/1999 | Roby et al. | 528/310 |
| 5,919,893 | A | 7/1999 | Roby et al. | 525/411 |
| 5,925,720 | A | 7/1999 | Kataoka et al. | 525/523 |
| 5,932,299 | A | 8/1999 | Katoot | 427/508 |
| 5,955,509 | A | 9/1999 | Webber et al. | 514/772.7 |
| 5,958,385 | A | 9/1999 | Tondeur et al. | 424/61 |
| 5,962,138 | A | 10/1999 | Kolluri et al. | 428/411.1 |
| 5,971,954 | A | 10/1999 | Conway et al. | 604/96 |
| 5,980,928 | A | 11/1999 | Terry | 424/427 |
| 5,980,972 | A * | 11/1999 | Ding | 427/2.24 |
| 5,997,517 | A | 12/1999 | Whitbourne | 604/265 |
| 6,010,530 | A | 1/2000 | Goicoechea | 623/1 |
| 6,011,125 | A | 1/2000 | Lohmeijer et al. | 525/440 |
| 6,013,854 | A | 1/2000 | Moriuchi | |
| 6,015,541 | A | 1/2000 | Greff et al. | 424/1.25 |
| 6,033,582 | A | 3/2000 | Lee et al. | 216/37 |
| 6,034,204 | A | 3/2000 | Mohr et al. | 528/328 |
| 6,042,875 | A | 3/2000 | Ding et al. | 427/2.24 |
| 6,051,576 | A | 4/2000 | Ashton et al. | 514/255 |
| 6,051,648 | A | 4/2000 | Rhee et al. | 525/54.1 |
| 6,054,553 | A | 4/2000 | Groth et al. | 528/335 |
| 6,056,993 | A | 5/2000 | Leidner et al. | 427/2.25 |
| 6,060,451 | A | 5/2000 | DiMaio et al. | 514/13 |
| 6,060,518 | A | 5/2000 | Kabanov et al. | 514/781 |
| 6,080,488 | A | 6/2000 | Hostettler et al. | 428/423.3 |
| 6,096,070 | A | 8/2000 | Ragheb et al. | 623/1 |
| 6,099,562 | A | 8/2000 | Ding et al. | 623/1.46 |
| 6,110,188 | A | 8/2000 | Narciso, Jr. | 606/153 |
| 6,110,483 | A | 8/2000 | Whitbourne et al. | 424/423 |
| 6,113,629 | A | 9/2000 | Ken | 623/1.1 |
| 6,120,491 | A | 9/2000 | Kohn et al. | 604/502 |
| 6,120,536 | A | 9/2000 | Ding et al. | 623/1.43 |
| 6,120,788 | A | 9/2000 | Barrows | 424/426 |
| 6,120,904 | A | 9/2000 | Hostettler et al. | 428/423.3 |
| 6,121,027 | A | 9/2000 | Clapper et al. | 435/180 |
| 6,129,761 | A | 10/2000 | Hubbell | 623/11 |
| 6,136,333 | A | 10/2000 | Cohn et al. | 424/423 |
| 6,143,354 | A | 11/2000 | Koulik et al. | 427/2.24 |
| 6,153,252 | A | 11/2000 | Hossainy et al. | 427/2.3 |
| 6,159,978 | A | 12/2000 | Myers et al. | 514/252.1 |
| 6,165,212 | A | 12/2000 | Dereume et al. | 623/1.13 |
| 6,172,167 | B1 | 1/2001 | Stapert et al. | 525/420 |
| 6,177,523 | B1 | 1/2001 | Reich et al. | 525/459 |
| 6,180,632 | B1 | 1/2001 | Myers et al. | 514/252.1 |
| 6,203,551 | B1 | 3/2001 | Wu | 606/108 |
| 6,211,249 | B1 | 4/2001 | Cohn et al. | 514/772.1 |
| 6,214,901 | B1 | 4/2001 | Chudzik et al. | 523/113 |
| 6,231,600 | B1 | 5/2001 | Zhong | 623/1.42 |
| 6,240,616 | B1 | 6/2001 | Yan | 29/527.2 |
| 6,245,753 | B1 | 6/2001 | Byun et al. | 514/56 |
| 6,245,760 | B1 | 6/2001 | He et al. | 514/234.8 |
| 6,248,129 | B1 | 6/2001 | Froix | 623/1.42 |
| 6,251,136 | B1 | 6/2001 | Guruwaiya et al. | 623/1.46 |
| 6,254,632 | B1 | 7/2001 | Wu et al. | 623/1.15 |
| 6,258,121 | B1 | 7/2001 | Yang et al. | 623/1.46 |
| 6,258,371 | B1 | 7/2001 | Koulik et al. | 424/422 |
| 6,262,034 | B1 | 7/2001 | Mathiowitz et al. | 514/44 |
| 6,270,788 | B1 | 8/2001 | Koulik et al. | 424/423 |
| 6,273,913 | B1 | 8/2001 | Wright et al. | |
| 6,277,449 | B1 | 8/2001 | Kolluri et al. | 427/289 |
| 6,283,947 | B1 | 9/2001 | Mirzaee | 604/264 |
| 6,283,949 | B1 | 9/2001 | Roorda | 604/288.02 |
| 6,284,305 | B1 | 9/2001 | Ding et al. | 427/2.28 |
| 6,287,628 | B1 | 9/2001 | Hossainy et al. | 427/2.3 |
| 6,299,604 | B1 | 10/2001 | Ragheb et al. | 604/265 |
| 6,306,166 | B1 | 10/2001 | Barry et al. | |
| 6,306,176 | B1 | 10/2001 | Whitbourne | 623/23.59 |
| 6,331,313 | B1 | 12/2001 | Wong et al. | 424/427 |
| 6,335,029 | B1 | 1/2002 | Kamath et al. | |
| 6,344,035 | B1 | 2/2002 | Chudzik et al. | 604/265 |
| 6,346,110 | B2 | 2/2002 | Wu | 606/108 |
| 6,346,119 | B1 | 2/2002 | Kuwahara et al. | |
| 6,358,556 | B1 | 3/2002 | Ding et al. | 427/2.24 |
| 6,379,381 | B1 | 4/2002 | Hossainy et al. | 623/1.42 |
| 6,387,379 | B1 | 5/2002 | Goldberg et al. | 424/400 |
| 6,395,326 | B1 | 5/2002 | Castro et al. | 427/2.24 |
| 6,419,692 | B1 | 7/2002 | Yang et al. | 623/1.15 |
| 6,451,373 | B1 | 9/2002 | Hossainy et al. | 427/2.25 |
| 6,482,834 | B2 | 11/2002 | Spada et al. | 514/311 |
| 6,494,862 | B1 | 12/2002 | Ray et al. | 604/96.01 |
| 6,503,538 | B1 | 1/2003 | Chu et al. | 424/497 |
| 6,503,556 | B2 | 1/2003 | Harish et al. | 427/2.24 |
| 6,503,954 | B1 | 1/2003 | Bhat et al. | 514/772.2 |
| 6,506,437 | B1 | 1/2003 | Harish et al. | 427/2.25 |
| 6,524,347 | B1 | 2/2003 | Myers et al. | |
| 6,527,801 | B1 | 3/2003 | Dutta | 623/1.46 |
| 6,527,863 | B1 | 3/2003 | Pacetti et al. | 118/500 |
| 6,528,526 | B1 | 3/2003 | Myers et al. | 214/311 |
| 6,530,950 | B1 | 3/2003 | Alvarado et al. | 623/1.13 |
| 6,530,951 | B1 | 3/2003 | Bates et al. | 623/1.45 |
| 6,540,776 | B2 | 4/2003 | Sanders Millare et al. | 623/1.15 |
| 6,544,223 | B1 | 4/2003 | Kokish | 604/103.01 |
| 6,544,543 | B1 | 4/2003 | Mandrusov et al. | 424/422 |
| 6,544,582 | B1 | 4/2003 | Yoe | 427/2.24 |
| 6,555,157 | B1 | 4/2003 | Hossainy | 427/2.24 |
| 6,558,733 | B1 | 5/2003 | Hossainy et al. | 427/2.24 |
| 6,565,659 | B1 | 5/2003 | Pacetti et al. | 118/500 |
| 6,572,644 | B1 | 6/2003 | Moein | 623/1.11 |
| 6,585,755 | B2 | 7/2003 | Jackson et al. | 623/1.15 |
| 6,585,765 | B1 | 7/2003 | Hossainy et al. | 623/1.45 |
| 6,585,926 | B1 | 7/2003 | Mirzaee | 264/400 |
| 6,605,154 | B1 | 8/2003 | Villareal | 118/500 |
| 6,616,765 | B1 | 9/2003 | Wu et al. | 623/1.45 |
| 6,623,448 | B2 | 9/2003 | Slater | 604/95.01 |
| 6,625,486 | B2 | 9/2003 | Lundkvist et al. | 604/21 |
| 6,645,135 | B1 | 11/2003 | Bhat | 600/3 |
| 6,645,195 | B1 | 11/2003 | Bhat et al. | 604/528 |
| 6,656,216 | B1 | 12/2003 | Hossainy et al. | 623/1.13 |
| 6,656,506 | B1 | 12/2003 | Wu et al. | 424/489 |
| 6,660,034 | B1 | 12/2003 | Mandrusov et al. | 623/1.42 |
| 6,663,662 | B2 | 12/2003 | Pacetti et al. | 623/1.13 |
| 6,663,880 | B1 | 12/2003 | Roorda et al. | 424/423 |
| 6,666,880 | B1 | 12/2003 | Chiu et al. | 623/1.11 |
| 6,673,154 | B1 | 1/2004 | Pacetti et al. | 118/500 |
| 6,673,385 | B1 | 1/2004 | Ding et al. | 427/2.28 |
| 6,689,099 | B2 | 2/2004 | Mirzaee | 604/107 |
| 6,695,920 | B1 | 2/2004 | Pacetti et al. | 118/500 |
| 6,706,013 | B1 | 3/2004 | Bhat et al. | 604/96.01 |
| 6,709,514 | B1 | 3/2004 | Hossainy | 118/52 |
| 6,712,845 | B2 | 3/2004 | Hossainy | 623/1.42 |
| 6,713,119 | B2 | 3/2004 | Hossainy et al. | 427/2.25 |
| 6,716,444 | B1 | 4/2004 | Castro et al. | 424/422 |
| 6,723,120 | B2 | 4/2004 | Yan | 623/1.15 |
| 6,723,121 | B1 | 4/2004 | Zhong | |

| | | | |
|---|---|---|---|
| 6,733,768 B2 | 5/2004 | Hossainy et al. ............ 424/426 |
| 6,740,040 B1 | 5/2004 | Mandrusov et al. ......... 600/439 |
| 6,743,462 B1 | 6/2004 | Pacetti ....................... 427/2.24 |
| 6,749,626 B1 | 6/2004 | Bhat et al. ..................... 623/1.1 |
| 6,753,071 B1 | 6/2004 | Pacetti et al. ................ 428/212 |
| 6,758,859 B1 | 7/2004 | Dang et al. .................. 623/1.15 |
| 6,759,054 B2 | 7/2004 | Chen et al. ................... 424/423 |
| 6,764,505 B1 | 7/2004 | Hossainy et al. ........... 623/1.15 |
| 7,056,550 B2 | 6/2006 | Davila et al. |
| 7,108,701 B2 | 9/2006 | Evens et al. |
| 7,217,286 B2 | 5/2007 | Falotico et al. |
| 7,223,286 B2 | 5/2007 | Wright et al. |
| 7,229,473 B2 | 6/2007 | Falotico et al. |
| 7,261,735 B2 | 8/2007 | Llanos et al. |
| 7,591,844 B2 | 9/2009 | Llanos et al. |
| 6,746,773 C1 | 7/2010 | Llanos et al. |
| 2001/0007083 A1 | 7/2001 | Roorda ......................... 623/1.15 |
| 2001/0014717 A1 | 8/2001 | Hossainy et al. ................ 525/60 |
| 2001/0018469 A1 | 8/2001 | Chen et al. .................... 523/121 |
| 2001/0020011 A1 | 9/2001 | Mathiowitz et al. ............ 514/44 |
| 2001/0029351 A1 | 10/2001 | Falotico et al. .......... 604/103.02 |
| 2001/0037145 A1 | 11/2001 | Guruwaiya et al. ......... 623/1.15 |
| 2001/0051608 A1 | 12/2001 | Mathiowitz et al. ............ 514/44 |
| 2002/0005206 A1 | 1/2002 | Falotico et al. .............. 128/898 |
| 2002/0007213 A1 | 1/2002 | Falotico et al. .............. 623/1.21 |
| 2002/0007214 A1 | 1/2002 | Falotico ....................... 623/1.21 |
| 2002/0007215 A1 | 1/2002 | Falotico et al. .............. 623/1.21 |
| 2002/0009604 A1 | 1/2002 | Zamora et al. ............... 428/450 |
| 2002/0016625 A1 | 2/2002 | Falotico et al. .............. 623/1.13 |
| 2002/0032414 A1 | 3/2002 | Ragheb et al. ............... 604/265 |
| 2002/0032434 A1 | 3/2002 | Chudzik et al. ............ 604/890.1 |
| 2002/0051730 A1 | 5/2002 | Bodnar et al. ................. 422/33 |
| 2002/0071822 A1 | 6/2002 | Uhrich ...................... 424/78.37 |
| 2002/0077693 A1 | 6/2002 | Barclay et al. ............... 623/1.13 |
| 2002/0082679 A1 | 6/2002 | Sirhan et al. ................. 623/1.15 |
| 2002/0087123 A1 | 7/2002 | Hossainy et al. ............. 604/198 |
| 2002/0091433 A1 | 7/2002 | Ding et al. ..................... 623/1.2 |
| 2002/0094440 A1 | 7/2002 | Llanos et al. ................. 428/421 |
| 2002/0111590 A1 | 8/2002 | Davila et al. .................. 604/265 |
| 2002/0120326 A1 | 8/2002 | Michal ......................... 623/1.15 |
| 2002/0123801 A1 | 9/2002 | Pacetti et al. ................ 623/1.46 |
| 2002/0142039 A1 | 10/2002 | Claude ......................... 424/486 |
| 2002/0155212 A1 | 10/2002 | Hossainy ..................... 427/2.25 |
| 2002/0165608 A1 | 11/2002 | Llanos et al. ................. 623/1.45 |
| 2002/0176849 A1 | 11/2002 | Slepian ......................... 424/93.7 |
| 2002/0183581 A1 | 12/2002 | Yoe et al. .......................... 600/3 |
| 2002/0188037 A1 | 12/2002 | Chudzik et al. .............. 523/112 |
| 2002/0188277 A1 | 12/2002 | Roorda et al. ................ 604/523 |
| 2003/0004141 A1 | 1/2003 | Brown ........................... 514/152 |
| 2003/0028243 A1 | 2/2003 | Bates et al. ................... 623/1.15 |
| 2003/0028244 A1 | 2/2003 | Bates et al. ................... 623/1.15 |
| 2003/0031780 A1 | 2/2003 | Chudzik et al. ................ 427/2.1 |
| 2003/0032767 A1 | 2/2003 | Tada et al. .................... 528/310 |
| 2003/0036794 A1 | 2/2003 | Ragheb et al. .............. 623/1.15 |
| 2003/0039689 A1 | 2/2003 | Chen et al. .................... 424/468 |
| 2003/0040712 A1 | 2/2003 | Ray et al. ...................... 604/173 |
| 2003/0040790 A1 | 2/2003 | Furst ............................. 623/1.11 |
| 2003/0059520 A1 | 3/2003 | Chen et al. ..................... 427/2.1 |
| 2003/0060877 A1 | 3/2003 | Falotico et al. .............. 623/1.42 |
| 2003/0065377 A1 | 4/2003 | Davila et al. ................. 623/1.13 |
| 2003/0072868 A1 | 4/2003 | Harish et al. ................ 427/2.24 |
| 2003/0073961 A1 | 4/2003 | Happ ............................. 604/274 |
| 2003/0083646 A1 | 5/2003 | Sirhan et al. ................. 604/891.1 |
| 2003/0083739 A1 | 5/2003 | Cafferata ..................... 623/1.42 |
| 2003/0097088 A1 | 5/2003 | Pacetti ............................ 604/19 |
| 2003/0097173 A1 | 5/2003 | Dutta ............................. 623/1.38 |
| 2003/0099712 A1 | 5/2003 | Jayaraman ................... 424/486 |
| 2003/0105518 A1 | 6/2003 | Dutta ............................ 623/1.38 |
| 2003/0113439 A1 | 6/2003 | Pacetti et al. ................ 427/2.24 |
| 2003/0150380 A1 | 8/2003 | Yoe ............................... 118/423 |
| 2003/0157241 A1 | 8/2003 | Hossainy et al. ........... 427/2.24 |
| 2003/0158517 A1 | 8/2003 | Kokish ..................... 604/103.01 |
| 2003/0190406 A1 | 10/2003 | Hossainy et al. ........... 427/2.25 |
| 2003/0207020 A1 | 11/2003 | Villareal ...................... 427/2.24 |
| 2003/0211230 A1 | 11/2003 | Pacetti et al. ................ 427/2.24 |
| 2004/0018296 A1 | 1/2004 | Castro et al. ................. 427/2.25 |
| 2004/0029952 A1 | 2/2004 | Chen et al. .................... 514/449 |
| 2004/0047978 A1 | 3/2004 | Hossainy et al. ............. 427/2.1 |
| 2004/0047980 A1 | 3/2004 | Pacetti et al. ................ 427/2.25 |
| 2004/0052858 A1 | 3/2004 | Wu et al. ...................... 424/490 |
| 2004/0052859 A1 | 3/2004 | Wu et al. ...................... 424/490 |
| 2004/0054104 A1 | 3/2004 | Pacetti .......................... 526/242 |
| 2004/0060508 A1 | 4/2004 | Pacetti et al. ................. 118/264 |
| 2004/0062853 A1 | 4/2004 | Pacetti et al. .................. 427/2.1 |
| 2004/0063805 A1 | 4/2004 | Pacetti et al. ................. 523/113 |
| 2004/0071861 A1 | 4/2004 | Mandrusov et al. ......... 427/2.24 |
| 2004/0072922 A1 | 4/2004 | Hossainy et al. ............. 523/113 |
| 2004/0073298 A1 | 4/2004 | Hossainy ..................... 623/1.46 |
| 2004/0086542 A1 | 5/2004 | Hossainy et al. ............. 424/423 |
| 2004/0086550 A1 | 5/2004 | Roorda et al. ................ 424/448 |
| 2004/0096504 A1 | 5/2004 | Michal .......................... 424/471 |
| 2004/0098117 A1 | 5/2004 | Hossainy et al. ............ 623/1.42 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 627 226 | 12/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 950 386 | 10/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| FR | 2 785 812 | 5/2000 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/38687 | 9/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |

| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

Anonymous, *Cardiologists Draw-Up The Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. :144, 7-32 (1999).
Inoue et al., *An AB block copolymer of oligo(methyl methacrylate) and poly(acryfic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(a-amino acid)a,w-Alkylene Diesters, and Aliphatic Dicarbolic Acids*, Journal of Polymer Science, Part A: Polymer Chemistry, 37(4), 391-407 (1999).
Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*; Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising α-Amino Acid, 1,2-Ethanediol, and Adipic Acid*, Chemistry Letters, pp. 21-24, (1991).
Shigeno, *Prevention of Cerebrovascular Spasm By Bosentan, Novel Endothelin Receptor*, Chemical Abstract 125:212307 (1996).
van Beusekom et al., *Coronary stent coatings*, Coronary Artery Disease 5(7):590-596 (Jul. 1994).
Wilensky et al, *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery, to a solid tumor*, Journal of Controlled Release 50:79-92 (1998).
Claude Tournut (1997) Chapter 31, "Thermoplastic Copolymers of Vinylidene Fluoride," John Scheirs, ed. *Modern Fluoropolymers*, pp. 577-596, Chichester, England, John Wiley & Sons Ltd.

* cited by examiner

POLYMERIC COATING FOR REDUCING THE RATE OF RELEASE OF A THERAPEUTIC SUBSTANCE FROM A STENT

BACKGROUND OF THE INVENTION

1. Field of the Invention

A medical device, such as a stent, for delivering a therapeutic substance is disclosed. The stent includes a polymeric coating for reducing the rate of release of the therapeutic substance.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

Depending on the physiological mechanism targeted, the therapeutic substance may be required to be released at an efficacious concentration for an extended duration of time. Increasing the quantity of the therapeutic substance in the polymeric coating can lead to poor coating mechanical properties, inadequate coating adhesion, and overly rapid rate of release. Increasing the quantity of the polymeric compound by producing a thicker coating can perturb the geometrical and mechanical functionality of the stent as well as limit the procedures for which the stent can be used.

It is desirable to increase the residence time of a substance at the site of implantation, at a therapeutically useful concentration, without the addition of a greater percentage of the therapeutic substance to the polymeric coating and without the application of a significantly thicker coating.

SUMMARY OF THE INVENTION

The present invention discloses a stent for delivery of a therapeutic agent. The stent includes a polymer coating for reducing the rate of release of the therapeutic agent. The polymer has a crystalline lattice structure, wherein the polymer is capable of significantly maintaining the crystalline lattice structure while the therapeutic agent is released from the stent such that the aqueous environment to which the stent is exposed subsequent to the implantation of the stent does not significantly convert the crystalline lattice structure of the polymer to an amorphous structure.

The coating can contain the therapeutic agent. In one embodiment, the melting point of the polymer is greater than or equal to about 135° C. at ambient pressure. In another embodiment, the polymer is a hydrophobic polymer having a solubility parameter not greater than about $10.7 \, (cal/cm^3)^{1/2}$.

Also disclosed is a method of forming a coating for a stent. The method includes applying a first composition including a polymeric material to at least a portion of the stent to form a polymer coating supported by the stent. The polymer has a crystalline structure, wherein the aqueous environment to which the coating is exposed subsequent to the implantation of the stent does not significantly convert the crystalline structure of the polymer to an amorphous structure for the duration of time which the agent is released from the stent.

The present invention additionally discloses a composition for coating a stent. The composition includes a fluid and a polymer dissolved in the fluid. The polymer includes a crystalline structure during the duration of delivery of an active agent from the stent, and the aqueous environment to which the stent is exposed subsequent to the implantation procedure does not significantly change the crystalline structure to an amorphous structure.

Also disclosed is a stent for delivering a therapeutic agent to an implanted site. The stent includes a radially expandable body structure and a polymeric coating supported by the body structure for extending the residence time of the therapeutic agent at the implanted site. The polymeric coating is made from a hydrophobic polymer having a degree of crystallinity that remains at or above about 10% at least until a significant amount of the therapeutic substance has been released from the stent.

DETAILED DESCRIPTION

Embodiments of the Rate-Reducing Coating

One mechanism through which the release rate of an active agent from a medical device can be controlled is the crystallinity of the polymer with which the medical device is coated. A polymer in which the molecules are arranged in a highly ordered and regular pattern formed by folding and stacking of the polymer chains is said to be crystalline. By contrast, amorphous polymers have molecules that are arranged randomly with no regularity of orientation with respect to one another. Among the factors that affect polymer crystallinity are the stereoregularity of the polymer, the tacticity of the polymer, the presence of branching, the degree of polymerization, and the strength of the intermolecular forces between the polymer chains.

The structural arrangement and regularity of a polymer is an important factor in the determination of polymer crystallinity. A regular arrangement along the polymer chains provides the polymer structure with a high degree of symmetry, allowing the chains to pack into crystals. Irregularity along the polymer chains, however, prevents the chains from packing closely to one another, thereby decreasing crystallinity. Polymers with regular, linear, and rigid structures tend to form ordered crystals. By contrast, polymers with large side groups, mixed tacticity or an atactic structure, a mix of side or functional groups, or composed of more than one monomer tend not to pack well into crystalline structures.

The degree of polymerization also contributes to the determination of the crystallinity of a polymer. Relatively short chains organize themselves into crystalline structures more readily than longer molecules, as longer molecules tend to become tangled and thus have difficulty arranging themselves in an ordered manner, resulting in a more amorphous structure.

Also influencing polymer crystallinity is the presence of intermolecular forces. The presence of polar and hydrogen bonding groups favors crystallinity because such groups promote dipole-dipole and hydrogen bonding intermolecular forces. Such strong interchain forces hold the polymer chains in a tightly packed configuration, thereby promoting crystallinity. By contrast, polymers with little or no intermolecular forces will tend to have random, non-crystalline structures as a result of thermal motion.

Typically, as the crystallinity of a polymer increases, so too does the polymer's ability to reduce the rate at which an active agent is released from a medical device coated with the polymer. This is because it is more difficult for an active agent to diffuse through a tightly packed, crystalline polymer than a more loosely packed, amorphous polymer. The purpose of the coating of the present invention is to decrease the rate of release of an active agent therefrom. Accordingly, the polymer for forming the rate-reducing coating should be selected to have sufficient crystallinity such that the active agent may not readily diffuse therethrough.

The degree of crystallinity of the polymer can be measured by the amount of the polymer that is in the form of crystallites or a detectable pattern of crystals as may be observed using conventional techniques such as x-ray diffraction, measurement of specific volume, infrared spectroscopy, and thermal analysis. For use with the embodiments of the present invention, the polymer can have a crystallinity of not less than about 10%, alternatively not less than about 25%. In accordance with another embodiment the degree of crystallinity should not be less than about 50%. When exposed to an aqueous environment such as blood, the polymer can have a crystallinity of not less than about 10%, alternatively not less than 25%. In one example, the polymer can have a crystallinity of at least 50% or at least 25% in an aqueous environment, such as in contact with blood.

In addition, the crystalline polymers for use in the rate-reducing coating of the present invention should be capable of maintaining their crystallinity in the aqueous in vivo environment in which the coated medical device will be employed. The crystallinity of some polymers decreases when exposed to water. This is due to absorption of water by the polymer, which is also known as polymer swelling. The absorbed water can reduce or eliminate the polymer crystallinity. In extreme cases, such absorption can lead to complete dissolution of the polymer. Polymers that contain ionic, polar, or hydrogen bonding groups have the potential to absorb water. In general, if the interaction of the polymer with water is stronger than that of the polymer with itself or of water with itself, the polymer will swell with water. When a polymer swells, its chains move apart to form pores in the polymeric network, thereby increasing the diffusion rate of an active agent through the polymeric network. Accordingly, the polymers for use in the rate-reducing coating of the present invention should be selected to maintain their crystallinity, and thus their rate-reducing capabilities, in an aqueous environment.

Many crystalline polymers that are hydrophobic can maintain their crystallinity in an aqueous environment because hydrophobic materials are "water-avoiding." One method of defining the hydrophobicity of a polymer is by the solubility parameter of the polymer, also known as the polymer's cohesive energy density. The solubility parameter is represented by Equation 1:

$$\delta = (\Delta E/V)^{1/2} \quad \text{(Equation 1)}$$

where
$\delta$=solubility parameter $((cal/cm^3)^{1/2})$
$\Delta E$=energy of vaporization (cal)
$V$=molar volume $(cm^3)$
("Polymer Handbook", 2nd Ed., Brandrup J. and E H Immergut, ed., Wiley-Interscience, John Wiley & Sons, N.Y. (1975)). Because polymers are typically non-volatile and thus cannot be vaporized without decomposition, the solubility parameter is measured indirectly. Briefly, solvents in which a polymer dissolves without a change in heat or volume are identified. The solubility parameter of the polymer is then defined to be the same as the solubility parameters of the identified solvents.

As a general rule, the value of the solubility parameter $\delta$ is inversely proportional to the degree of hydrophobicity of a polymer. Polymers that are very hydrophobic may have a low solubility parameter value. This general proposition is particularly applicable for polymers having a glass transition temperature below physiological temperature. A polymer that is sufficiently hydrophobic for use in the rate-limiting membrane of the present invention can have a solubility parameter of not more than about 10.7 $(cal/cm^3)^{1/2}$. Representative examples of such crystalline, hydrophobic polymers include polytetrafluoroethylene, ethylene-tetrafluoroethylene copolymer, fluoroethylene-alkyl vinyl ether copolymer, polyhexafluoropropene, low density linear polyethylenes having high molecular weights, ethylene-olefin copolymers, styrene-ethylene-styrene block copolymers, styrene-butylene-styrene block copolymers, styrene-ethylene/butylene-styrene block copolymers, styrene-butadiene-styrene block copolymers, styrenic block copolymers including KRATON™ polymers (available from KRATON™ Polymers, Houston, Tex.), ethylene-anhydride copolymers, ethylene-acrylic acid copolymers, poly (vinylidene fluoride), ethylene methacrylic acid copolymers, polyurethanes with a polydimethylsiloxane soft segment, poly(vinylidene fluoride-co-hexafluoropropene), and polycarbonate urethanes (e.g., BIONATE 55D and BIONATE 75D).

Polymers of relatively high crystallinity can also maintain their crystallinity in an aqueous environment. Highly crystalline polymers are typically rigid, have high melting temperatures, and are minimally affected by solvent penetration. Since the degree and strength of crystallinity of a polymer can be roughly approximated by the melting temperature of the polymer, sufficiently high crystallinity for use with the present invention is possessed by polymers having a melting temperature greater than or equal to about 135° C. at ambient pressure. Representative examples of polymers having a melting temperature of at least 135° C. at ambient pressure include, but are not limited to, nylon 6, poly (vinylidene fluoride), poly (vinylidene fluoride-co-hexafluoropropene), polytetrafluoroethylene, polyetheretherketone (PEEK), polyimide, polysulfone, ethylene-co-methacrylic acid, ethylene-co-acrylic acid, and styrenic block copolymers including KRATON™ polymers (available from KRATON™ Polymers, Houston, Tex.).

The above-described suitably crystalline polymers can be used to form a rate-reducing coating onto a medical device. The embodiments of the composition for such a coating can be prepared by conventional methods wherein a predetermined amount of a suitable polymeric compound is added to a predetermined amount of a compatible solvent. "Solvent" is defined as a liquid substance or composition that is mutually compatible with a polymer and is capable of significantly dissolving the polymer at the concentration desired in the composition. Examples of solvents include, but are not limited to, dimethylsulfoxide (DMSO), chloroform, acetone, xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, hexafluoroisopropanol, methylene chloride, hexamethylphosphorous triamide, N-methylmorpholine, trifluoroethanol, formic acid, and phenol. The polymeric compound can be added to the solvent at ambient pressure and under anhydrous atmosphere. The polymeric compound is soluble before crystallization in a solvent system at, for example, temperatures of less than or equal to about 80° C. If necessary, gentle heating and stirring and/or mixing can be employed to effect dissolution of the polymer into the solvent, for example 12 hours in a water bath at about 60° C.

Application of the composition can be by any conventional method, such as by spraying the composition onto the device or by immersing the device in the composition. Operations such as wiping, centrifugation, blowing, or other web-clearing acts can also be performed to achieve a more uniform coating. Briefly, wiping refers to physical removal of excess composition from the surface of the stent; centrifugation refers to rapid rotation of the stent about an axis of rotation; and blowing refers to application of air at a selected pressure to the deposited composition. Any excess composition can also be vacuumed off of the surface of the device. The solvent is removed from the composition to form the rate-reducing coating by allowing the solvent to evaporate. The evaporation can be induced by heating the device at a predetermined temperature for a predetermined period of time. For example, the device can be heated at a temperature of about 60° C. for about 1 hour to about 12 hours. The heating can be conducted in an anhydrous atmosphere and at ambient pressure and should not exceed the temperature that would adversely affect the active agent. The heating can, alternatively, be conducted under a vacuum condition. It is understood that essentially all of the solvent will be removed from the composition, but traces or residues may remain blended with the polymer.

Examples of the Device

A medical device for use in conjunction with the above-described rate-reducing coating is broadly defined to include any inter- or intraluminal device used for the release of an active agent and/or for upholding the luminal patency in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, anastomosis devices such as axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Use of the Rate-Reducing Coating

In one embodiment, the above-described rate-reducing coating, free from therapeutic substances or active agents, can function as a barrier layer through which an underlying therapeutic substance or active agent must diffuse to be released from a device into a treatment site. The active agent can be carried by the device, such as in porous cavities in the surface of the device, or can be impregnated in a reservoir polymer layer formed beneath the rate-reducing coating. Such a rate-reducing barrier coating can be of any suitable thickness. The thickness of the coating can be from about 0.01 microns to about 20 microns, more narrowly from about 0.1 microns to about 10 microns. By way of example, the rate-reducing barrier coating can have a thickness of about 3 microns.

In another embodiment, the rate-reducing coating can additionally function as a reservoir for carrying the therapeutic substance or active agent. In such an embodiment, sufficient amounts of an active agent can be dispersed in the blended composition of the suitably crystalline polymer and the solvent. The polymer can comprise from about 0.1% to about 35%, more narrowly from about 2% to about 20% by weight of the total weight of the composition, the solvent can comprise from about 59.9% to about 99.8%, more narrowly from about 79% to about 89% by weight of the total weight of the composition, and the active agent can comprise from about 0.1% to about 40%, more narrowly from about 1% to about 9% by weight of the total weight of the composition.

The active agent should be in true solution or saturated in the blended composition. If the active agent is not completely soluble in the composition, operations including mixing, stirring, and/or agitation can be employed to effect homogeneity of the residues. The active agent may be added so that the dispersion is in fine particles.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Exposure of the active agent to the composition should not adversely alter the active agent's composition or characteristic. Accordingly, the particular active agent is selected for compatibility with the solvent or blended polymer-solvent.

In one embodiment, an optional primer layer can be formed on the outer surface of the medical device. Formation of a primer layer, free from any active agents, can be by any conventional method, such as by spraying a primer composition containing a polymer and a compatible solvent onto the medical device or immersing the medical device in the primer composition followed by evaporation of the solvent. The polymer selected can be any polymer suitable for coating a medical device. With the use of thermoplastic polymers such as, but not limited to, ethylene vinyl alcohol copolymer, poly-caprolactone, poly(lactide-co-glycolide), and poly(hydroxy-butyrate), the deposited primer composition should be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of a stent. The medical device should be exposed to the heat treatment for any suitable duration of time that will allow for the formation of the primer layer on the outer surface of the device and for the evaporation of the solvent employed. It is understood that essentially all of the solvent will be removed from the primer composition but traces or residues can remain blended with the polymer.

In other embodiments, the crystalline coating can be top-coated with one or more additional coating layers. Such additional coating layers can be for increasing the biocompatibility of the device. For example, in one embodiment, the additional coating layer can be formed from ethylene vinyl alcohol (EVAL), polyethylene glycol, polyethylene oxide, hyaluronic acid, heparin, or heparin derivatives having hydrophobic counterions, thereby providing biocompatibility to the outermost, tissue-contacting surface of the medical device.

In another embodiment, an additional coating layer can serve as yet another rate-reducing layer. Because the additional rate-reducing layer does not contain active agents, the methods by which such a layer is deposited is not limited to the methods by which the polymer layers having active agents are applied. Therefore, in addition to application by conventional methods, such as by spraying a polymeric composition onto the device or by immersing the device in a polymeric composition, the additional rate-reducing layers can be deposited by physical vapor deposition (PVD) techniques, which are known to one of ordinary skill in the art. Representative examples of barrier materials that can be deposited via PVD techniques include plasma-deposited polymers, parylene C, parylene N, parylene D, perfluoro parylene, tetrafluoro (AF4) parylene, metallic layers, metallic oxides, metal carbides, and metal nitrides.

Methods of Use

In accordance with embodiments of the above-described method, an active agent can be applied to an implantable medical device or prosthesis, e.g., a stent, retained on the stent during delivery and expansion of the stent, and released at a desired control rate and for a predetermined duration of time at the site of implantation. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the invention will be illustrated by the following set forth prophetic examples, which are being given by way of illustration only and not by way of limitation. All parameters are not to be construed to unduly limit the scope of the embodiments of the invention.

Example 1

A 2% (w/w) solution of EVAL in dimethylacetamide (DMAC) is applied to a 13 mm Tetra™ stent (available from Guidant Corporation) using an EFD 780S spray device (available from EFD Inc., East Providence, R.I.) until 50 micrograms of solids have been deposited onto the stent. The stent is baked at 140° C. for 60 minutes to form a primer layer on the stent. A solution of 1:9 (w/w) actinomycin D:EVAL and 2% (w/w) EVAL in DMAC is sprayed onto the primered stent until 100 micrograms of solids have been deposited. The stent is baked at 50° C. for 2 hours to form an actinomycin D-containing reservoir coating. A 2% (w/w) polyvinylidene fluoride solution in DMAC is sprayed until 300 micrograms of solids have been deposited onto the stent. The stent is baked at 50° C. for 2 hours to form a crystalline rate-reducing membrane of polyvinylidene fluoride.

Example 2

A 2% (w/w) solution of EVAL in DMAC is applied to a 13 mm Tetra™ stent using an EFD 780S spray device until 50 micrograms of solids have been deposited onto the stent. The stent is baked at 140° C. for 60 minutes to form a primer layer on the stent. A solution of 1:3 (w/w) dexamethasone:poly(ethylene-co-vinyl-acetate) and 2% (w/w) poly(ethylene-co-vinyl-acetate) in cyclohexanone is sprayed onto the primered stent until 300 micrograms of solids have been deposited. The stent is baked at 60° C. for 2 hours to form a dexamethasone-containing reservoir coating. A 2% (w/w) KRATON G1650 (available from KRATON™ Polymers, Houston, Tex.) solution in xylene is sprayed until 300 micrograms of solids have been deposited onto the stent. The stent is baked at 60° C. for 2 hours to form a crystalline rate-reducing membrane of KRATON G1650.

Example 3

A 2% (w/w) solution of EVAL in DMAC is applied to a 13 mm Tetra™ stent using an EFD 780S spray device until 50 micrograms of solids have been deposited onto the stent. The stent is baked at 140° C. for 60 minutes to form a primer layer on the stent. A solution of 1:2 (w/w) estradiol:EVAL and 2% (w/w) EVAL in DMAC is sprayed onto the primered stent until 350 micrograms of solids have been deposited. The stent is baked at 60° C. for 2 hours to form an estradiol-containing reservoir coating. A 2% (w/w) poly(vinylidene fluoride-co-hexafluoropropene) solution in 1:1 (w/w) acetone:DMAC is sprayed until 300 micrograms of solids have been deposited onto the stent. The stent is baked at 60° C. for 2 hours to form a crystalline rate-reducing membrane of poly(vinylidene fluoride-co-hexafluoropropene).

Example 4

A 2% (w/w) solution of poly(n-butyl methacrylate) in 4:1 (w/w) acetone:cyclohexanone is applied to a 13 mm Tetra™ stent using an EFD 780S spray device until 50 micrograms of solids have been deposited onto the stent. The stent is baked at 70° C. for 60 minutes to form a primer layer on the stent. A solution of 1:2 (w/w) etoposide:EVAL and 2% (w/w) EVAL in DMAC is sprayed onto the primered stent until 300 micrograms of solids have been deposited. The stent is baked at 60° C. for 2 hours to form an etoposide-containing reservoir coating. A 1.5% (w/w) silicone-urethane Elast-Eon™ 55D (available from Elastomedic Pty Ltd., Australia) solution in 1:1 (w/w) THF:DMAC is sprayed until 300 micrograms of solids have been deposited onto the stent. The stent is baked at 60° C. for 2 hours to form a crystalline rate-reducing membrane of silicone-urethane Elast-Eon™ 55D.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A stent for delivery of a therapeutic agent, comprising:
a substrate;
a polymer coating on the substrate that substantially reduces the rate of release of the therapeutic agent, the polymer having a crystalline structure with a crystallinity of not less than about 25%, wherein the polymer is capable of significantly maintaining the crystalline structure while the therapeutic agent is released from the stent such that the aqueous environment to which the stent is exposed subsequent to the implantation of the stent does not significantly convert the crystalline structure of the polymer to an amorphous structure such that the crystallinity of the polymer is not less than about 25% when exposed to the aqueous environment subsequent to the implantation of the stent,
wherein the polymer having a crystalline structure is selected from a group consisting of fluoroethylene-alkyl vinyl ether copolymer, low density linear polyethylenes having high molecular weights, ethylene-olefin copolymers, styrene-ethylene-styrene block copolymers, styrene-butylene-styrene block copolymers, styrene-ethylene/butylene-styrene block copolymers, styrene-butadiene-styrene block copolymers, ethylene-anhydride copolymers, styrenic block copolymers, ethylene methacrylic acid copolymers, polyurethanes with a polydimethylsiloxane soft segment, and nylon 6; and
a primer layer ormed on a surface of the substrate, wherein the polymer coating is formed over the primer layer, and wherein the primer layer acts as an adhesive tie between the polymer coating and the surface of the stent.

2. The stent of claim 1, wherein the crystallinity of the polymer is not less than about 50% prior to the implantation of the stent.

3. The stent of claim 1, wherein the melting point of the polymer is greater than or equal to about 135° C. at ambient pressure.

4. The stent of claim 1, wherein the polymer is a hydrophobic polymer having a solubility parameter of not more than about 10.7 $(cal/cm^3)^{1/2}$.

5. The stent of claim 1, wherein the coating contains the therapeutic agent for delivery of the therapeutic agent.

6. The stent of claim 1, additionally comprising:
a reservoir layer containing the therapeutic agent formed on the primer layer, wherein the coating is formed on at least a portion of the reservoir layer to reduce the rate of release of the therapeutic agent.

7. The stent of claim 1, wherein the polymer coating comprises a second coating layer over a first coating layer, the first coating layer being a reservoir layer containing a therapeutic agent above the substrate, and the second coating layer being free from therapeutic agents.

8. A method of forming a coating for a stent that substantially reduces the rate of release of a therapeutic agent from the stent, comprising:
forming a primer layer on the stent;
applying a composition including a polymeric material to at least a portion of the stent to form a polymer coating supported by the stent, the polymer having a crystalline structure with a crystallinity of not less than 25%, wherein the aqueous environment to which the coating is exposed subsequent to the implantation of the stent does not significantly convert the crystalline structure of the polymer to an amorphous structure for the duration of time which the agent is released from the coating such that the crystallinity of the polymer is not less than about 25% when exposed to the aqueous environment subsequent to the implantation of the stent, wherein the polymer having a crystalline structure is selected from a group consisting of fluoroethylene-alkyl vinyl ether copolymer, low density linear polyethylenes having high molecular weights, ethylene-olefin copolymers, styrene-ethylene-styrene block copolymers, styrene-butylene-styrene block copolymers, styrene-ethylene/butylene-styrene block copolymers, styrene-butadiene-styrene block copolymers, ethylene-anhydride copolymers, styrenic block copolymers, ethylene methacrylic acid copolymers, polyurethanes with a polydimethylsiloxane soft segment, and nylon 6.

9. A stent comprising a polymeric coating, wherein the coating is produced using the method of claim 8.

10. The method of claim 8, wherein the crystallinity of the polymeric material is not less than about 25% during the release of the therapeutic agent from the stent.

11. The method of claim 8, wherein the polymeric material has a solubility parameter not more than about 10.7 $(cal/cm^3)^{1/2}$.

12. The method of claim 8, wherein the polymeric material has a melting point greater than or equal to about 135° C. at ambient pressure.

13. The method of claim 8, wherein the polymer coating comprises a second coating layer over a first coating layer, the first coating layer being a reservoir layer containing a therapeutic agent above the substrate, and the second coating layer being free from therapeutic agents.

14. A stent for delivering a therapeutic agent to an implanted site, comprising:
   a radially expandable body structure;
   a primer on a surface of the radially expandable body structure; and
   a polymeric coating supported by the body structure that substantially increases the residence time of the therapeutic agent at the implanted site, wherein the polymeric coating is made from a hydrophobic polymer having a degree of crystallinity that remains at or above about 10% at least until a significant amount of the therapeutic substance has been released from the stent,
   wherein the polymer having a degree of crystallinity that remains at or above about 10% is selected from a group consisting of fluoroethylene-alkyl vinyl ether copolymer, low density linear polyethylenes having high molecular weights, ethylene-olefin copolymers, styrene-ethylene-styrene block copolymers, styrene-butylene-styrene block copolymers, styrene-ethylene/butylene-styrene block copolymers, styrene-butadiene-styrene block copolymers, ethylene-anhydride copolymers, ethylene-acrylic acid copolymers, styrenic block copolymers, ethylene methacrylic acid copolymers, polyurethanes with a polydimethylsiloxane soft segment, and nylon 6.

15. The stent of claim 14, wherein the polymer coating comprises a second coating layer over a first coating layer, the first coating layer being a reservoir layer containing a therapeutic agent above the substrate, and the second coating layer being free from therapeutic agents.

16. A stent for delivery of a therapeutic agent, comprising:
   a substrate; and
   a polymer coating on the substrate that substantially reduces the rate of release of the therapeutic agent, the polymer having a crystalline structure with a degree of crystallinity of not less than about 10%, wherein the polymer is capable of significantly maintaining the crystalline structure while the therapeutic agent is released from the stent such that the aqueous environment to which the stent is exposed subsequent to the implantation of the stent does not significantly convert the crystalline structure of the polymer to an amorphous structure, and
   wherein the polymer is an ethylene-acrylic acid copolymer.

17. A method of forming a coating for a stent that substantially reduces the rate of release of a therapeutic agent from the stent, comprising:
   applying a composition including a polymeric material to at least a portion of the stent to form a polymer coating supported by the stent, the polymer having a crystalline structure with a degree of crystallinity of not less than about 10%, wherein the aqueous environment to which the coating is exposed subsequent to the implantation of the stent does not significantly convert the crystalline structure of the polymer to an amorphous structure for the duration of time which the agent is released from the coating, and
   wherein the polymer is an ethylene-acrylic acid copolymer.

18. A stent for delivery of a therapeutic agent, comprising:
   a substrate; and
   a polymer coating on the substrate that substantially reduces the rate of release of the therapeutic agent, the polymer having a crystalline structure with a crystallinity of not less than about 25%, wherein the polymer is capable of significantly maintaining the crystalline structure while the therapeutic agent is released from the stent such that the aqueous environment to which the stent is exposed subsequent to the implantation of the stent does not significantly convert the crystalline structure of the polymer to an amorphous structure such that the crystallinity of the polymer is not less than about 25% when exposed to the aqueous environment subsequent to the implantation of the stent,
   with the proviso of (1) a primer layer being under the coating, a barrier layer being over the coating, or both; or (2) wherein the polymer coating is a barrier layer disposed over a reservoir layer.

* * * * *